United States Patent [19]

Letchworth, III et al.

[11] Patent Number: 5,462,734
[45] Date of Patent: Oct. 31, 1995

[54] BOVINE HERPESVIRUS VACCINE AND METHOD OF USING SAME

[75] Inventors: Geoffrey J. Letchworth, III, Madison; Barbara A. Israel, Mount Horeb, both of Wis.

[73] Assignee: Wisconsin Alumni Research Foundation, Madison, Wis.

[21] Appl. No.: 35,558

[22] Filed: Mar. 22, 1993

Related U.S. Application Data

[63] Continuation of Ser. No. 607,794, Nov. 2, 1990, abandoned.

[51] Int. Cl.$^6$ .......................... A61K 39/245; C07K 14/03
[52] U.S. Cl. ...................... 424/229.1; 424/813; 530/395; 435/69.3
[58] Field of Search ........................... 424/88, 89, 229.1, 424/813; 530/395; 435/69.3

[56] References Cited

U.S. PATENT DOCUMENTS

| | | | |
|---|---|---|---|
| 5,151,267 | 9/1992 | Babiuk | 424/186.1 |
| 5,182,109 | 1/1993 | Tamura | 424/202.1 |

OTHER PUBLICATIONS

Gerber, J. D. et al. (1978) Am. J. Vet. Res. 39:753–760.
Tamura, S. et al. (1988) Vaccine 6:409–413.
Leary, T. P. et al. (1990) J. Immunol. 145:718–723.
McKercher, D. G. and G. L. Krenshaw, "Comparative Efficacy of Intranasally and Parenterally Administered Infectious Bovine Rhinotracheitis Vaccines," *J. Am. Vet. Med. Assoc.*, 159:1362–1369 (1971).
Stanberry, L. R. et al., "Genital Reinfection After Recovery from Initial Genital Infection with Herpes Simplex Virus Type 2 in Guinea Pigs," *J. Infect. Dis.*, 153:1055–1061 (1986).
Mertz, G. J., et al., "Double–Blind, Placebo–Controlled Trial of a Herpes Simplex Virus Type 2 Glycoprotein Vaccine in Persons at High Risk for Genital Herpes Infection," *J. Infect. Dis.* 161:653–660 (1990).
Israel, B. A., et al., "Epitope Specificity and Protective Efficacy of the Bovine Immune Response to Bovine Herpesvirus–1 Glycoprotein Vaccines," *Vaccine* 6:349–356 (1988).
Babiuk, L. A., et al., "Protection of Cattle from Bovine Herpesvirus Type 1 (BHV–1) Infection by Immunization with Individual Viral Glycoproteins," *Virology* 59: 57–66 (1987).
Straub, O. C. and I. C. Mawhinney, "Vaccination to Protect Calves Against Infectious Bovine Rhinotracheitis," The Veterinary Record, 122:407–411 (1988).
Ludwig, H. and J. P. Gregersen, "Infectious Bovine Rhinotracheitis/Infectious Pustular Vulvovaginitis: BHV–1 Infections," *Rev. Sci. Tech. Off. Int. Epiz.* 5[4]:869–878 (1986).
Marshall, R. L., et al., "Characterization of Envelope Proteins of Infectious Bovine Rhinotracheitis Virus (Bovine Herpesvirus 1) by Biochemical and Immunological Methods," *J. Virology*, 57[3]:457–753 (1986).
Whitbeck, J. C. et al., "Comparison of the Bovine Herpesvirus of gI Gene and the Herpes Simplex Virus Type 1 gB Gene," J. Virology, 62[9]: 3319–3327 (1988).
Misra, V., et al., "Sequence of a Bovine Herpesvirus Type 1 Glycoprotein, Gene that is Homologous to the Herpes Simplex Gene for the Glycoprotein gB," *Virology* 166:542–549 (1988).
Tikoo, S. K., et al., "Molecular Cloning, Sequencing, and Expression of Functional Bovine Herpesvirus 1 Glycoprotein gIV in Transfected Bovine Cells," *J. Virology* 64 [10] :5132–5142 (1990).
Fitzpatrick, D. R., et al., "Nucleotide Sequence of Bovine Herpesvirus Type 1 Glycoprotein gIII, a Structural Model for gIII as a New Member of the Immunoglobulin Superfamily, and Implications for the Homologous Glycoproteins of other Herpesviruses," *Virology* 173:46–57 (1989).
Waldman, R. H. et al., "Immunication Against Influenza," *JAMA* 207[3]: 520–524 (1969).
Liew, F. Y., et al., "Cross–protection in Mice Infected with Influenza A Virus by the Respiratory Route is Correlated with Local IgA Antibody Rather than Serum Antibody or Cytotoxic T Cell Reactivity," *Eur. J. Immunol.* 14:350–356 (1984).
Lycke, N. and J. Holmgren, "Strong Adjuvant Properties of Cholera Toxin on Gut Mucosal Immune Responses to Orally Presented Antigens," *Immunology* 59:301–308 (1986).
Tamura, S., et al., "Protection Against Influenza Virus Infection by Vaccine Inoculated Intranasally with Cholera Toxin B Subunit," Vaccine 6: 409–413 (1988).
Israel, B. A., et al., "Stimulation of a Protective Mucosal Immunity to Bovine Herpesvirus 1," in *Abstracts of Papers Presented at the 70th Annual Meeting of the Conference of Research Workers in Animal Disease*, Nov. 6–7, 1989.

*Primary Examiner*—Christine M. Nucker
*Assistant Examiner*—Julie Krsek-Staples
*Attorney, Agent, or Firm*—Quarles & Brady

[57] ABSTRACT

A vaccination kit and protocol for using it are disclosed which results in immunity from infection by herpesvirus. A first formulation of an isolated viral glycoprotein is injected intramuscularly to result in systemic immunity. Later a second formulation including the isolated viral glycoprotein with an adjuvant is administered intranasally, or otherwise administered to the mucosal membranes. A level of both systemic and mucosal immunity is achieved such that viral infection, as well as symptomatic disease, is avoided. The method and the vaccine are exemplified by a vaccine for Bovine Herpesvirus 1.

6 Claims, No Drawings

BOVINE HERPESVIRUS VACCINE AND METHOD OF USING SAME

This application is a continuation of application Ser. No. 07/607,794, filed Nov. 2, 1990, now abandoned.

FIELD OF THE INVENTION

The present invention relates to the field of viral vaccines in general and relates, in particular, to a vaccine for viruses of the Herpesvirus family and methods for introducing such vaccines into mammals such that not only are symptoms of the disease prevented but also virus infection and replication is prevented as well.

BACKGROUND OF THE INVENTION

Herpesviruses are a family of eukaryotic viruses associated with a variety of animal and human diseases, such as orolabial and genital herpes, chicken pox and Epstein-Barr disease. The Herpesvirus family is characterized by its double-stranded DNA and enveloped icosahedral virion, and a genomic size of the double-stranded DNA in the range of 120 to 230 kilobases. The Herpesvirus family is most commonly associated with disease of vertebrates.

Herpesviruses pose a unique challenge to the development of effective vaccines and vaccine administration protocols. These viruses characteristically initially infect epithelial cells on mucosal surfaces. Once a virus has infected an epithelial cell, it then replicates and may spread from cell to cell via intracellular bridges. Herpesviruses are thus capable of establishing a latent infection in neural ganglia and other locations without further exposure to the extracellular environment. Because most herpesvirus infections are initiated on a mucosal surface where systemic immune mechanisms are absent, and spread covertly through intracellular bridges, the generation of systemic immunity by parenteral vaccination has proven ineffective in preventing initial host infection by herpesviruses, although the severity of resulting disease can sometimes be modified through systemic vaccination.

Because of the adverse medical and economic effects from the diseases caused by the herpesviruses, there has been significant effort towards the development of vaccines for these viruses. Originally such efforts focused on whole viral agents, which were inactivated by chemical treatment of the virus or were attenuated by mutation or continuous passage in cell culture to achieve less virulent strains of the virus. Regardless of the outcome of vaccination, these approaches have severe limitations including potential oncogenicity that restrict the use of live or killed herpesviral vaccines in humans. Attenuated herpes virus vaccines cause side effects such as abortion, latency, and disease. Killed virus vaccines are often poorly immunogenic.

The Herpesvirus family, as with many eukaryotic viruses, has characteristic glycoproteins which are carried on the lipid bilayer envelope of the herpesvirus virion. Some of these glycoproteins are believed to function in the initial attachment of virus to cells and penetration of virus into cells. While the glycoproteins themselves do vary to some degree from virus strain to strain, and among the viruses specific to particular hosts, there is a large degree of conservation among the various members of the Herpesvirus family as exemplified by the 45.9% homology between the sequence for bovine herpesvirus 1 (BHV1) glycoprotein I and the human herpes simplex virus type 1 (HSV1) glycoprotein B, as reported by Whitbeck et al., *Jour. of Virology*, 62:9, pages 3319–3327 (1988). Similar homologies have been found in all other human herpesviruses, herpes simplex type 2, varicella-zoster, Epstein-Barr, cytomegalovirus, and human herpesvirus type 6, as well as all animal herpesviruses yet studied, bovine herpesvirus type 2, pseudorabies, Marek's disease virus, equine herpesvirus type 4, feline herpesvirus, and simian herpesvirus SA8.

Because it has previously been demonstrated that the neutralizing antibody responses produced in vertebrates following challenge with herpesvirus are specific to the glycoproteins carried on the envelope, it has been suggested that vaccines may be developed which include only the glycoproteins, and none of the remaining elements of the viruses necessary for virulence. Accordingly, efforts have been made to characterize, clone, and sequence the glycoproteins for use in creating such vaccines. Such vaccines based on glycoprotein immunogenic agents have also been tested as vaccines both in mammals and in humans. In humans, a vaccine based on a glycoprotein subunit from herpes simplex virus 2 (HSV2) was administered to individuals. Such vaccination elicited antibody titers to the proteins unevenly, but failed to provide effective protection from acquisition of viral infection. Mertz et al., *Jour. of Infectious Diseases,* 166, pp. 653–660 (1990).

Letchworth and Israel have previously utilized a glycoprotein vaccine from bovine herpesvirus 1, in an attempt to develop an effective vaccine for the BHV1 virus in cattle. Systemic administration of the glycoproteins engendered relatively high titers of serum neutralizing antibodies in the putatively immunized animals. Yet, upon intranasal challenge with virulent virus, these animals showed no resistance to infection or disease. Israel et al., *Vaccine* 6, pages 349–356 (1988). Thus this and many other herpesviral vaccination studies that were aimed at the generation of systemic neutralizing antibodies consistently proved insufficient to prevent introduction and proliferation of live viruses through the mucosal membranes, the normal portal of entry. In other words, while the vaccinated individual or animal may become less sick, or not sick, because of the vaccination, the individual or animal still becomes a host for the virus and therefore an infectious vector. Obviously such strategy may be useful for particular individuals, but is less than desirable on an epidemiological scale for prevention of wide spread viral disease.

The systemic immune system has been pivotal to the success of many non-herpesviral vaccines. No previous subunit viral vaccines have been focused on the generation or evaluation of the mucosal arm of the immune response. This response is partially independent of the systemic response and is comprised of lymphocytes that circulate between mucosal sites, respond to local antigenic stimuli, and secrete immunoglobulins A and G locally into the mucus. Systemic immunization, via the intravenous, intramuscular, or subcutaneous route does not necessarily evoke a mucosal response. Mucosal immunoglobulins, in contrast to systemic antibodies, are present on the exterior surface of the animal and can neutralize virus before it enters the animal. The mucosal immune system is thus designed to be evoked as the first line of defense against pathogens that enter through the mucosal surface.

In the particular example of a herpesvirus vaccine given in the specification below, the virus in question is Bovine Herpesvirus 1. Bovine Herpesvirus 1 (BHV1) is a ubiquitous pathogenic agent in cattle. As with other herpesviruses, it is an enveloped double-stranded DNA virus. In North America, BHV1 infection causes a respiratory disease known as infectious bovine rhinotracheitis. Infected animals may suffer weight loss, may abort fetuses, may have decreased productivity, and may die from complications of a secondary bacterial pneumonia known as "shipping fever." In Europe, BHV1 has been most commonly manifested as the genital disease infectious pustular vulvovaginitis, but the incidence of respiratory disease is increasing. BHV1 is transmitted by aerosol route, by direct contact, or through semen from infected bulls. While both modified live and killed virus BHV1 vaccines have been used for decades, the disease caused by BHV1 remains a major economic threat to the beef and dairy and artificial insemination industries world wide, since the vaccines have proven ineffective in preventing spread of virulent agents. Since BHV1 establishes latency in the infected hosts, a characteristic typical of herpesvirus in general, recrudescence with subsequent shedding of infectious virus and continued spread of virus to other susceptible animals may occur over the entire lifetime of an animal, even though the animal has an immune response induced by vaccination.

It is quite often the case in modern vaccine design that adjuvants may be introduced with the vaccine to increase immunogenic response to the immunizing agent. This can be the difference between a theoretical and a practical vaccination protocol because soluble glycoproteins are poor immunogens. Traditional adjuvants are formulated to stimulate the systemic and not the mucosal immune response.

SUMMARY OF THE INVENTION

The present invention is summarized in that a vaccine kit for immunization of animals against herpesviruses includes two vaccine formulations, the first formulation including a glycoprotein of the herpesvirus and a carrier and package for introduction parenterally, and the second formulation including a glycoprotein of the herpesvirus, an adjuvant capable of inducing a mucosal immune response with the glycoprotein, and a carrier, and being packaged for application to a mucosal surface of the patient.

The present invention is also summarized in a method of introducing vaccine to patients to induce both systemic and mucosal immunity to herpesvirus infection which includes the steps of first priming the patient with a vaccine formed of a glycoprotein or glycoproteins from the herpesvirus by parenteral vaccination, and secondly boosting the patient nasally or via other mucosal surfaces with a vaccine including a glycoprotein or glycoproteins from the herpesvirus together with an adjuvant capable of inducing heightened mucosal immune response in the patient.

It is an objective of the present invention to provide a vaccine capable of not only reducing disease caused by herpesvirus but also of preventing herpesvirus latency and replication so that viral spread is prevented.

It is another objective of the present invention to provide a protocol for vaccine introduction into individuals which provides both systemic and mucosal immunity to viral challenge.

It is a further objective of the present invention to provide both a vaccine and a protocol for using it which is safe, effective, efficient and economical to administer to susceptible patients, be they animal or human.

It is yet another objective of the present invention to provide a specific vaccine which is effective and economical to administer for the prevention of bovine herpesvirus 1 virus infection.

Other objectives, advantages, and features of the present invention will become apparent from the following specification.

DETAILED DESCRIPTION OF THE INVENTION

In accordance with the present invention, a kit for the vaccination of humans or animals to immunize them from herpesvirus infection, and a method for utilizing that vaccination kit is described by which immunity to viral infection and replication can be achieved in vaccinated individuals. It is to be understood that the objective is more than just inducing relative symptomatic attenuation of viral disease, it is to induce a full or partial immunity to viral infection and replication. In other words it is not only an objective that the vaccinated individuals remain free from disease when challenged by virulent agent, but also that the vaccinated individuals never become vectors or hosts for viral replication. The achievement of this objective insures that if a population is vaccinated, epidemiological spread of the disease can be drastically reduced.

In its simplest embodiment, the vaccine protocol of the present invention makes use of two vaccination formulations. The first formulation consists of a herpesviral glycoprotein or glycoproteins associated with immunogenic response in susceptible individuals, an optional adjuvant, and a carrier suitable for parenteral injection. The formulation should be substantially free of intact viral nucleic acid molecules capable of causing disease in susceptible individuals. This first vaccine formulation is thus intended for parenteral injection into the patient to induce a systemic immune response, and to induce the creation of circulating neutralizing antibodies specific to the antigenic glycoprotein in the vaccine formulation.

The second vaccine formulation includes again a quantity of the same glycoprotein or glycoproteins from the virus capable of inducing an immune response in the mucosal tissues of the susceptible individual, a carrier suitable for aerosol administration to a susceptible individual, and an adjuvant to heighten the mucosal immune response of the glycoprotein. Again, the formulation should not include any viral nucleic acid molecules capable of inducing disease in the individual. The second vaccine formulation is thus intended for aerosol or internasal administration to the susceptible individual, or other form of administration in which the glycoprotein application is directly to mucosal surfaces. The glycoprotein of the formulations includes at least one of the same glycoproteins administered through the systemic injection. The second vaccination protocol is administered after the first, following a time period for immune response, and may require more than one administration to achieve a desired level of immunity or resistance to initial viral infection and subsequent replication.

It has been found here by the investigators, somewhat surprisingly, that first introducing an antigenic agent to a patient systemically and then subsequently following up that first injection with the administration to mucosal surfaces of the same antigenic agent results in a heightened level of immunogenic response through the mucosal system than could be achieved by either route used alone. The addition of a mucosal adjuvant to the antigenic agent, when administered to the mucosal surfaces, results in even more heightened immunological response in the susceptible individuals. Through the use of this technique, it has now been found that not only can disease be effectively controlled in the susceptible individuals, but also viral replication can be diminished or eliminated completely.

It is specifically intended with regard to the herpesviruses which are the object of the vaccination protocol of the present invention, that live virus or killed or attenuated virus are not the most desired antigenic agent for use within the vaccination protocol of the present invention. The disadvantage of using such agents is the possibility, however slight, that virulent particles could be maintained at even a low frequency in an attenuated live virus vaccine or that occasional live, and virulent, viruses could be harbored within a killed virus vaccine. Since it has previously been demonstrated that the immunogenic response to herpesviruses is a result of antigenic recognition of the surface glycoproteins, it is proposed herewith that the vaccinating agent preferably be isolated glycoprotein or glycoproteins from a herpesvirus. It is therefore also preferred that the DNA from herpesvirus either be isolated from the glycoprotein, or digested to completion by an enzymatic agent, so that the vaccination formulation contains no live or replicable DNA sequences from the herpesvirus capable of inducing disease in the susceptible individual. Furthermore, use of one or a few viral glycoproteins in the vaccine will permit vaccinated animals to be distinguished from infected animals by simple serologic tests.

Broadly speaking, there are three approaches to methods for creating glycoprotein molecules for use with a vaccine in accordance with the present invention. One method is to culture virus in vitro, and then to recover the glycoprotein molecules from the virus. This is done by culturing the virus in suitable susceptible host cell in vitro culture, isolating the virus, and then isolating the glycoproteins from the virus. Since the glycoproteins of the herpesvirus are contained within the lipid envelope of the herpesvirus virion, it is possible to release glycoproteins from virus particles through detergent dissolution of the lipid envelopes surrounding the particles. Then it merely becomes necessary to isolate the glycoprotein molecules from the heterogeneous mixture containing the virus particles. Alternatively, viral glycoproteins are present on the surface of infected cells and may be isolated from detergent-solubilized lysates of infected cells, rather than from whole virions. These processes result in preparations containing mixtures of viral glycoproteins. Preparations of individual glycoproteins can be obtained by a number of techniques, among them being affinity chromatography based upon antibodies specific to the desired glycoprotein or glycoproteins. Described below, in connection with the BHV1 virus, are three separate hybridomas, each capable of synthesizing and secreting a monoclonal antibody specific to one of the three characteristic glycoproteins from BHV1. The techniques for using such monoclonal antibodies in affinity chromatography to isolate desired proteins or glycoproteins from heterogenous biological mixtures are techniques well known to those of ordinary skill in the art.

A second broad technique for the creation of similar glycoproteins is through the use of cloned DNA sequences, or genes, coding for the expression of the glycoproteins in recombinant protein production systems. It is merely necessary to have available the DNA sequences of the genes which code for the glycoproteins. For example, in connection with the BHV1 herpesvirus described below, complete DNA sequences for the glycoproteins gI, gIII and gIV are presented below in their entirety. Based on the information contained in the sequences below, it becomes possible to construct oligonucleotides to recreate the native viral coding sequences, or to create hybridization probes for isolating the genomic coding sequences from DNA from herpesviruses. Using any technique, once the coding region has been isolated or synthesized, it can be readily joined to appropriate regulatory sequences, such as promoters, translational enhancers, and translational and transcriptional terminators capable of coding the expression of the protein in other organisms. In order to achieve a glycosylation pattern characteristic of the desired glycoproteins, it is preferred that the expression system for the glycoprotein have a glycosylation pattern matching the host animal sought to be immunized. For most vertebrate systems it is sufficient if the expression of the protein be in a eukaryotic system, the glycosylation pattern being sufficiently similar among eukaryotes such that antigenically similar glycoproteins can be created in various eukaryotic systems while still retaining the specific antigenicity and the appropriate immune response in various vertebrate.

The third technique for the creation of glycoproteins is to chemically synthesize an amino acid chain with the appropriate protein sequence. It may not be necessary that it be glycosylated.

It is specifically envisioned that a vaccination kit may be constructed using the invention described herein which includes at least two forms of administration of the antigenic vaccination agent to the individual to be vaccinated. As described earlier, the two modes of administration are by injection, to obtain systemic response, and by application to mucosal membranes, such as through an inhalant. Thus the first formulation would include the immunogenic response inducing glycoproteins in injectable form, carried in a carrier, optionally along with a suitable adjuvant, also suitable for parenteral injection into an individual. The form of injection could be subcutaneous, intramuscular, or intradermal, although intramuscular and subcutaneous are most likely to be preferred. Such carriers and adjuvants are well known to the art, and no specific criteria on the selection of such a carrier is believed essential to the practice of the present invention. For the second vaccination formulation, that intended for mucosal administration, an adjuvant is also recommended. The same glycoprotein or glycoproteins is the vaccinating agent in the second formulation, and the carrier may be the same, or a different one, as deemed necessary or advisable for aerosol, or other method of application to mucosal membrane.

The choice of the specific adjuvant for use with the second vaccination formulation is subject to some variation. Several types of such adjuvants are available and are likely to be successful with the vaccination agents described in the present invention. The particular vaccination protocol, kit, and formulation described below for BHV1 utilizes an adjuvant of the non-toxic B subunit of the cholera toxin molecule, which was selected because of its commercial availability (Sigma). Other similar adjuvants are readily available and may be substituted freely. It is preferred that the adjuvant be one that is able to bind to epithelial cells and to stimulate mucosal immunity.

The practice of the present invention is described in particularity below in connection with the immunization of cattle to the Bovine Herpesvirus 1 (BHV1). It has previously been demonstrated that the BHV1 virus contains at least three different glycoproteins, referred to as gI, gIII and gIV. Each of those three different glycoproteins has been demonstrated to give rise to immunogenic responses in cattle. All have been previously utilized as the antigenic component of experimental vaccines intended for the induction of a systemic immunologic response, although only live attenuated and killed virus vaccines are currently marketed for protection against BHV1. The use of any of these three glycoproteins in a protocol in which only systemic immunity is induced will result in animals which, when exposed to the virulent BHV1 virus, may have attenuated or minimal symptoms of the disease, but which will nevertheless become hosts for virus infection and replication. The DNA sequences coding for the protein components of the three glycoproteins have all been published, and the sequences are available to those of ordinary skill in the art. The sequence of gI is contained in Misra et al., *Virology*, 166, pages 542–549 (1988) and Whitbeck, *Jour. of Virology*, 62:9, pages 3319–3327 (1988). The DNA sequence of the glycoprotein gIII is contained in Fitzpatrick et al., *Virology*, 173, pages 46–57 (1989). The complete DNA sequence of the glycoprotein gIV has recently been published by Tikoo et al., *Jour. of Virology*, 64:10, pages 5132–5142 (1990). It has been found that the DNA sequences of these glycoproteins, when expressed in eukaryotic cell expression systems, result in glycoproteins which are immunogenically identical or very similar to the native glycoproteins isolated from virus particles, and therefore suitable for use as vaccinating agents within the present invention.

It is to be understood that while the example of the utility of the present invention is described below in connection with the BHV1 virus, that logic behind the design of this protocol, and its demonstrated utility in inducing immunity to viral infection and replication, is applicable to the Herpesvirus family of viruses. While there is some host specificity among the members of the Herpesvirus family, there is also a great deal of conservation of sequence and there is, in fact, significant conservation between the sequences of the various glycoproteins from the BHV1 virus and those which have been isolated from human viruses, notably human herpes simplex-1 virus and other human and animal herpesviruses. Despite differences that confer host specificity, the glycoproteins function in a similar fashion and antibodies act against them similarly. Therefore, it is logical to assume that the two-step dosage protocol and vaccine formulation system described herein will be equally effective in other vertebrate hosts, such as humans, as it has been demonstrated below to be in bovine. The antigenic vaccine agents of the present invention, that is to say the isolated glycoproteins from the herpesviral particles, can equally well be created for other members of the herpesvirus family, other than the BHV1 described in detail below.

EXAMPLES

Preparation of Glycoproteins from Virions

The Cooper-1 (Colorado-1) strain of BHV1 was obtained from the American Type Culture Collection, plaque purified and propagated at low multiplicity of infection on Madin-Darby bovine kidney cells (MDBK), which may also be obtained from the ATCC, accession code CCL22. The cells were grown in minimum essential medium (MEM, Gibco) supplemented with fetal calf serum.

To prepare viral envelope glycoproteins, Madin-Darby kidney cells were infected with virus at a multiplicity of infection 0.05. Forty-eight hours after infection, virus was recovered from the culture supernatant by centrifugation at 100,000 x g at 4° C. for 1 hour through a 30% sucrose cushion. The pelleted virus was resuspended in lysis buffer (0.15M NaCl 0.005M EDTA, 0.5% NP40, 0.5% deoxycholate, 2 mM PMSF) and incubated at 4° C. for 15 minutes. The lysed virus material was layered onto 30% sucrose and centrifuged at 100,000 x g at 4° C. for 1 hour. The solubilized proteins remaining near the top of the sucrose were treated for 10 minutes at 37° C. with one unit of DNAse/$10^6$ pfu virus, to degrade any DNA remaining in the solution.

Preparation of Recombinant Glycoprotein

The complete DNA sequence of the gI glycoprotein is given below and may be found in Whitbeck et al., *Jour. Virology*, 62:9, pp. 3319–3327 (1988) and in Misra et al., *Virology*, 166, pp. 542–549 (1988). A complete protein coding sequence for the gI protein was obtained, and the gene was inserted in a bovine papilloma virus vector, pNeoBPV$_{100}$, a mammalian cell expression vector. The vector with the gI coding insert was transfected into bovine fibroblasts cultured in vitro. The fibroblast cells produced correctly glycosylated gI glycoprotein which was recovered by affinity chromatography. Bovine fibroblasts expressing recombinant glycoprotein I were harvested, pelleted by low-speed centrifugation and lysed in a buffer containing 50 mM Tris pH 8.0, 5 mM EDTA, 0.15 M NaCl, 0.2 mM PMSF and 0.5% Nonidet P-40 (BRL) for 10 minutes at 4° C. The lysate was then centrifuged at 10,000 g for 30 minutes at 4° C. to remove cell debris and the supernatant fluid was then cleared of subcellular particles by centrifugation at 100,000 g for 1 hour at 4C. The cleared lysate was passed through a column of Sepharose 4B coupled to monoclonal antibody 5106. The bound gI was eluted with 0.05M diethylamine, dialyzed against water and concentrated by vacuum centrifugation and stored at −70° C.

Hypothetically, the given sequences for gIII and gIV may be inserted similarly into mammalian cell expression vectors and transfected into cells in culture so that purified gIII and gIV glycoproteins can be produced and recovered by a process similar to that used with gI above. Specific monoclonal antibodies to be used for isolation of the BHV1 glycoproteins gI, gIII and gIV are available. For glycoprotein gI a monoclonal designated 5106 was used as produced by hybridoma 510604.2.9, which has been deposited with the ATCC, 12301 Parklawn Drive, Rockville, Md. 20852, as Accession No. HB10579. Monoclonal 1106 produced by hybridoma 110604.1.12, ATCC Accession No. HB10577, is specific to the gIV glycoprotein. The gIII glycoprotein is selected by monoclonal antibody mAb 2905 produced by hybridoma 290504.1.11 ATCC Accession No. HB10578.

Vaccination Series 1

Seronegative bull calves were vaccinated in one of two protocols. Four calves were vaccinated intranasally by aerosol spray and two calves were vaccinated by an intramuscular injection followed by two subsequent intranasal spray applications separated at two week intervals. The dosages of each mode of exposure was 100 µg protein per dose, of combined viral glycoproteins prepared from virus cultured in vitro as described above.

Nasal secretions of the calves were then examined for the presence of antibody to BHV1 by viral plaque reduction assay, by isotype-specific indirect fluorescent antibody staining of BHV1 infected cells incubated with nasal secretions, and by the ability of nasal secretions to immunoprecipitate viral glycoproteins from a radiolabeled infected cell lysate. Only secretions from the calves which had received an intramuscular injection prior to nasal administration contained detectable levels of BHV1 specific IgA antibodies.

Vaccination Series 2

To test whether this protocol could be used to induce resistance to viral infection, a second series was performed. Four calves were vaccinated with an initial intramuscular dose of 100 µg of the mixed glycoprotein vaccine emulsified in incomplete Freund's adjuvant. The animals were then dosed intranasally with the same formulation 2 weeks later. A group of four calves served as controls and were vaccinated with detergent solubilized, DNAse treated extract of Madin-Darby kidney cells.

On days two and five following intranasal vaccine administration, nasal swabs were collected from each calf and assayed in cell culture for the presence of any infectious virus. No infectious virus could be recovered from any animal confirming that the vaccine was free of infectious virus. To test for the development of mucosal immunity, the level of BHV1 specific antibodies in nasal secretions was monitored. Following vaccination, BHV1 antibodies were detectable but remained at low levels.

To boost the mucosal immune response, an adjuvant was desired. Cholera toxin has been reported to stimulate mucosal immune response against non-replicating unrelated antigens, and has been used in mice to induce immunity to Sendai and influenza virus infections. The non-toxic B subunit of cholera toxin (CTB) was chosen due to its ability to bind to mucosal epithelial cells and its ready commercial availability (Sigma).

To prepare an enhanced intranasal vaccine, 20 μg of CTB was mixed with 100 μg of mixed envelope BHV1 glycoproteins in phosphate buffered saline. This formulation was administered to the test calves intranasally followed by a booster dose two weeks later of the glycoproteins alone.

The test results of this second intranasal administration was that the animals had a dramatic increase in the titer of IgA specific to BHV1 in nasal secretions. In two animals the increase was greater than 100-fold. Tests were conducted to determine the specific targets for the induced IgA produced, and it was found that two of the vaccinated calves produced antibodies to all of gI, gIII and gIV, while the other two had detectable levels of IgA specific only to gI.

To test the immunity of the vaccinated animals, the vaccinated and control calves were all challenged with an intranasal aerosol of $3\times10^5$ plaque forming units of virulent BHV1. Nasal swabs were collected daily from the animals to assay for infectious virus by culture on MDBK cells. The results are summarized in Table 1 below, which illustrates that the control calves continued to shed virus while the vaccinated animals shed none or, at most, very little virus. To verify that the virus was absent and not merely neutralized by the antibodies, the nasal swab material was analyzed by polymerase chain reaction (PCR) assay for viral DNA. Viral DNA was detected in samples from all four control calves but in none of the samples from vaccinated calves.

TABLE 1

BHV1 in Nasal Secretions From Challenged Calves

| | Controls | | | | Vaccination | | | |
|---|---|---|---|---|---|---|---|---|
| Day | 127 | 130 | 484 | 492 | 41 | 480 | 481 | 489 |
| 1 | — | — | — | — | — | — | — | — |
| 2 | 3.8 | 2.8 | 4.8 | — | — | — | — | — |
| 3 | ND | 4.3 | 4.3 | 1.8 | — | — | 2.8 | — |
| 4 | 4.8 | 4.8 | 6.3 | 1.8 | — | — | — | — |
| 5 | 4.3 | 5.8 | 4.3 | 2.8 | — | — | — | — |
| 6 | 4.8 | 5.3 | 4.3 | 5.8 | — | — | — | — |
| 7 | 6.3 | 6.3 | 3.8 | 3.3 | 2.8 | — | — | — |
| 8 | 4.3 | 5.3 | 2.8 | 3.3 | — | — | — | — |
| 9 | 3.3 | 6.8 | 2.3 | 1.8 | — | — | — | — |
| 10 | 5.3 | 5.8 | — | — | — | — | — | — |

In this table, the values represent the log base 10 TCID 50 recovered per nasal swab, with "_" indicating none detected.

To determine if the mucosal immunity had prevented the establishment of latent infection in the vaccinated and challenged calves, they were then immunosuppressed 10 weeks after viral challenge by seven daily intramuscular injections of 40 mg of dexamethasone. All control animals had a recrudescence of BHV1 infection and shed virus in nasal secretions. Two of the vaccinated calves (480 and 486) had no recrudescence, although the other two animals did have recrudescence and shed virus.

Vaccination Series 3

The use of a mixture of the three glycoproteins as a vaccine has a slight disadvantage in that it does not permit ready serological distinction between immunized and infected animals. It was determined that it would be useful to test if a vaccination program based on a single glycoprotein would be effective.

The glycoprotein gI was selected, which happens to have DNA sequence homology with the gB glycoprotein of HSV1 and 2. The glycoprotein was produced recombinantly, as described above, in a bovine fibroblast culture.

Five test calves received an initial intramuscular dose of 25 μg of gI in incomplete Freund's adjuvant, followed two weeks later by an administration of an intranasal spray of 25 μg of gI combined with 20 μg of CTB. Three control calves were mock vaccinated with lysate of a cell line transfected with a bovine papilloma virus vector without the gI insert. Two successive intranasal boosters of 10 μg of gI alone were also administered to the test calves at two week intervals.

After this administration, three of the five vaccinated calves developed antibodies to BHV1 in both serum and nasal secretions, while two calves (Numbers 149 and 152) did not. Based on this, a booster immunization of 50 μg of gI was administered intramuscularly and a 50 μg dose of gI was administered intranasally. The titers of antibody to BHV1 in vaccinated and control calves is presented below in Table 2, where the values in the first row represent the reciprocal of the highest dilution of serum showing neutralization of 100 $TCID_{50}$ of BHV1 on Madin-Darby kidney cells, while the values in the second two rows represent the reciprocal of the highest dilution of nasal secretions giving a positive value in an ELISA assay.

TABLE 2

Serological Status of Calves

| | Controls | | | Vaccinated | | | | |
|---|---|---|---|---|---|---|---|---|
| | 140 | 141 | 146 | 145 | 147 | 149 | 151 | 152 |
| Serum | <4 | <4 | <4 | 256 | 128 | 16 | 128 | 32 |
| Nasal IgA | <2 | <2 | <2 | 256 | 64 | 8 | 256 | 8 |
| Nasal IgG | <2 | <2 | <2 | 128 | 32 | 32 | 128 | 16 |

This demonstrates that all vaccinated animals had antibody to BHV1, while controls did not.

The calves were then challenged after ten weeks by intranasal aerosol of $5\times10^5$ pfu of BHV1. All three control calves shed large quantities of BHV1 over an 11 day period. In contrast, the virus could not be detected by culture on MDBK in the nasal secretions from four out of five of the vaccinated calves. The other calf did shed virus, but only on two of the eleven test days. These results are presented in Table 3, where the values are the reciprocal log 10 of dilution of nasal swab samples causing cytopathology on Madin-Darby kidney cells.

TABLE 3

BHV 1 Recovered in Nasal Secretions of Calves Following Challenge

| | Controls | | | Vaccinates | | | | |
|---|---|---|---|---|---|---|---|---|
| Days | 141 | 140 | 146 | 145 | 147 | 149 | 151 | 152 |
| 1 | — | — | — | — | — | — | — | — |
| 2 | 4.8 | 3.3 | 5.3 | — | — | — | — | — |
| 3 | 6.3 | 3.3 | 5.3 | — | — | — | — | — |
| 4 | 6.8 | 6.3 | 5.3 | — | — | — | — | 3.3 |
| 5 | 7.8 | 5.8 | 7.3 | — | — | — | — | — |
| 6 | 7.3 | 7.8 | 6.8 | — | — | — | — | — |
| 7 | 7.8 | 7.8 | 7.8 | — | — | — | — | 3.3 |
| 8 | 7.8 | 7.8 | 6.8 | — | — | — | — | — |
| 9 | 6.3 | 7.3 | 5.3 | — | — | — | — | — |
| 10 | 4.3 | 6.8 | — | — | — | — | — | — |
| 11 | 3.8 | 5.8 | — | — | — | — | — | — |
| 12 | — | 5.3 | — | — | — | — | — | — |

Again the animals were immunosuppressed with dexamethasone to test for recrudescence. All controls shed virus but no recrudescence or viral shedding could be detected in the vaccinated animals.

Thus it has been demonstrated that this vaccination protocol provides an effective level of immunity to viral infection and replication. This offers the potential for epidemiological control of herpesviruses since viral replication and shedding as well as symptoms of disease and establishment of latent infections can be prevented.

Below are presented three DNA sequences, Seq. ID No.:1, Seq. ID No.:2, and Seq. ID No.:3, which are the DNA sequences of the coding regions from BHV-1 for the glycoproteins gI, gIII, and gIV. It is to be appreciated that these sequences are reproduced here from sequences published by others. Accordingly, while faithful reproduction of the published sequences has been intended here, and while the sequences are believed generally correct, there may be occasional errors in nucleotide bases or amino acid identifications due either to sequencing errors or clerical errors in publication or reproduction here. Nevertheless, the sequences are believed sufficiently accurate for practical utility in reproducing these glycoproteins.

We claim:

1. A method for the induction of acquired immunity to bovine herpesvirus 1 (BHV1) comprising the steps of
   (a) introducing a quantity of a first vaccination formulation so as to induce a systemic immunological response, the first vaccination formulation including glycoprotein gI from the BHV1 capable of causing a systemic immune response and a carrier suitable for parenteral administration, the first formulation being substantially free of viral DNA; and
   (b) exposing the mucosal membranes to a second vaccination formulation so as to induce an immunological response in the mucosal tissues, the second vaccination formulation including glycoprotein gI from BHV1 capable of causing a mucosal immune response, an adjuvant comprising the B subunit from cholera toxin effective to increase the mucosal immune response to the glycoprotein, and a carrier suitable for application to mucosal tissues, the second formulation being substantially free of viral DNA.

2. A method as in claim 1 wherein the glycoprotein gI used in the vaccination formulations is isolated from whole virus or virus-infected cells.

3. A method as in claim 1 wherein the glycoprotein gI used in the vaccination formulations is produced recombinantly in a eukaryotic cell system in culture.

4. A method as in claim 1 wherein the introduction of the first formulation is accomplished by intramuscular, subcutaneous, intradermal, or intraperitoneal injection.

5. A method as in claim 1 wherein exposing the mucosal membranes to the second formulation is accomplished by intranasal inhalant.

6. A vaccination kit for inducing acquired immunity to BHV1 comprising
   (a) a first vaccination formulation comprising a quantity of isolated glycoprotein gI from BHV1 effective to induce a systemic immune response and a carrier suitable for parenteral administration, the formulation being substantially free of viral DNA; and
   (b) a second vaccination formulation comprising a quantity of isolated glycoprotein gI from BHV1 effective to induce a mucosal immune response, an adjuvant comprising the B subunit of cholera toxin capable of enhancing the mucosal immune response to the glycoprotein, and a carrier suitable for introduction to the mucosal membranes, the formulation being substantially free of viral DNA.

* * * * *

UNITED STATES PATENT AND TRADEMARK OFFICE
CERTIFICATE OF CORRECTION

PATENT NO. : 5,462,734

DATED : October 31, 1995

INVENTOR(S) : Geoffrey J. Letchworth, III
Barbara A. Israel

It is certified that error appears in the above-identified patent and that said Letters Patent is hereby corrected as shown below:

Page 2, column 1, line 7, before the paragraph commencing "Field of the Invention" should be inserted the following as a new paragraph:

This invention was made with United States Government support awarded by USDA, Grant #83-CRSR-2-2202, 96-CRSR-2-2902, 87-CRCR-1-2548, 88-37277-3946 and Hatch Funds. The United States Government has certain rights in this invention.--

Signed and Sealed this

Twelfth Day of March, 1996

*Attest:*

BRUCE LEHMAN

*Attesting Officer*   Commissioner of Patents and Trademarks

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 3519 base pairs
( B ) TYPE: nucleic acid
( C ) STRANDEDNESS: double
( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
( A ) ORGANISM: bovine herpervirus- 1
( B ) INDIVIDUAL ISOLATE: P8-2 strain ( v i i ) FEATURE:
( A ) NAME/KEY: coding sequence for gI glycoprotein
( B ) LOCATION: 379 to 3165
( C ) IDENTIFICATION METHOD: sequence analysis ( x ) PUBLICATION INFORMATION:
( A ) AUTHORS: Misra, Vikram
Nelson, Randy
Smith, Michael
( B ) TITLE: Sequence of a Bovine Herpesvirus Type-1 etc.
( C ) JOURNAL: Virology
( D ) VOLUME: 166
( F ) PAGES: 542-549
( G ).DATE: 1988
( K ) RELEVANT RESIDUES IN SEQ ID NO:1: FROM 379 TO 3165

( x i ) SEQUENCE DESCRIPTION:SEQ ID NO:1:

ACGGGCCGCT CTTTGACGGC AGCGCGCACA ACTTCGCGCA GCGCCAAACA CCGCGCTGTA 60

CTTTAGCGTG GAAAACGTGG GCCTGCTCCC GCACCTCAAG GAGGAGCTGG CCGCGTTTAT 120

GCTGGCGGCC GCGGGGGGCG GGTGGGCGGT AAGCGACTTC CAGCAGTTTT TTTGCTTCGC 180

ATCCGCGCGG GCNCGGGCGT CACCGCCGCG CAGCGGCTCG CCTGGCAATA TATCCGCGAG 240

-continued

| | | | | | | | | | | |
|---|---|---|---|---|---|---|---|---|---|---|
| CTCGTTCTGG | CCCGCGCCGT | CTTTGCGTCC | GTCTTCCACT | GCGGACGCCG | TCCCGCTGCT | | | | | 300 |
| GCGTGCGGAC | CGAACGGCCG | CCGGGCCCGG | ACGGCGGCAG | TCGTGTCCCA | GCGGCGTCTA | | | | | 360 |

```
CCTGACCTAC GAGGAGTC ATG GCC GCT CGC GGC GGT GCT GAA CGC GCC GCG GGC      414
                        Met Ala Ala Arg Gly Gly Ala Glu Arg Ala Ala Gly
                                         5                         10

GCC GGA GAC GGT CGG CGA GGA CAG CGT CGT CAT CTA CGA CCG GGA CGT          462
Ala Gly Asp Gly Arg Arg Gly Gln Arg Arg His Leu Arg Pro Gly Arg
         15                  20                  25

GTT CTC GCT GCT CTA CGC GGT CCT GCA GCG CCT GGC GCC GGG GCG              510
Val Leu Ala Ala Leu Arg Gly Pro Ala Ala Pro Gly Ala Gly Gly Ala
         30                  35                  40

CGC GCC GCG CTA GCC GCT GCC CTG CTA TGG GCG ACG TGG GCC CTG CTG          558
Arg Ala Ala Leu Ala Ala Ala Leu Leu Trp Ala Thr Trp Ala Leu Leu
45                  50                  55                  60

CTG GCG GCG CCC GCC GCG GGG CGA CCG GCG ACA ACG CCC CCG GCG CCC          606
Leu Ala Ala Pro Ala Ala Gly Arg Pro Ala Thr Thr Pro Pro Ala Pro
                 65                  70                  75

CCG CCC GAA GAG GCC GCG AGC CCG GCG CCC CCG GCG AGC CCC AGC CCC          654
Pro Pro Glu Glu Ala Ala Ser Pro Ala Pro Pro Ala Ser Pro Ser Pro
             80                  85                  90

CCC GGC CCC GAC GGC GAC GAC GCC GCC AGC CCC GAC AAC AGC ACA GAC          702
Pro Gly Pro Asp Gly Asp Asp Ala Ala Ser Pro Asp Asn Ser Thr Asp
         95                 100                 105

GTG CGC GCC GCG CTC CGG CTC GCG CAG GCG GCC GGG GAA AAC TCG CGC          750
Val Arg Ala Ala Leu Arg Leu Ala Gln Ala Ala Gly Glu Asn Ser Arg
110                 115                 120

TTC TTC GTG TGC CCG CCG CCC TCG GGC GCC ACG GTG GTC CGG CTC GCG          798
Phe Phe Val Cys Pro Pro Pro Ser Gly Ala Thr Val Val Arg Leu Ala
125                 130                 135                 140

CCC GCG CGG CCG TGC CCT GAG TAC GGG CTC GGG CGG AAC TAC ACG GAG          846
Pro Ala Arg Pro Cys Pro Glu Tyr Gly Leu Gly Arg Asn Tyr Thr Glu
                145                 150                 155

GGC ATC GGC GTC ATT TAC AAG GAG AAC ATC GCG CCG TAC ACG TTC AAG          894
Gly Ile Gly Val Ile Tyr Lys Glu Asn Ile Ala Pro Tyr Thr Phe Lys
             160                 165                 170

GCC ATC ATT TAC TAC AAA AAC GTG ATC GTG ACC ACG ACC TGG GCG GGC          942
Ala Ile Ile Tyr Tyr Lys Asn Val Ile Val Thr Thr Thr Trp Ala Gly
         175                 180                 185

AGC ACG TAC GCG GCC ATT ACA AAC CAG TAC ACG GAC CGC GTG CCC GTG          990
Ser Thr Tyr Ala Ala Ile Thr Asn Gln Tyr Thr Asp Arg Val Pro Val
190                 195                 200

GGC ATG GGC GAG ATC ACG GAC CTG GTG GAC AAG AAG TGG CGC TGC CTT         1038
Gly Met Gly Glu Ile Thr Asp Leu Val Asp Lys Lys Trp Arg Cys Leu
205                 210                 215                 220

TCG AAA GCC GAG TAC CTG CGC AGC GGG CGC AAG GTG GTG GCC TTT GAC         1086
Ser Lys Ala Glu Tyr Leu Arg Ser Gly Arg Lys Val Val Ala Phe Asp
                225                 230                 235

CGC GAC GAC GAC CCC TGG GAG GCG CCG CTG AAG CCT GCG CGG CTG AGC         1134
Arg Asp Asp Asp Pro Trp Glu Ala Pro Leu Lys Pro Ala Arg Leu Ser
             240                 245                 250

GCG CCC GGG GTG CGG GGC TGG CAC ACG ACG GAC GAT GTG TAC ACG GCG         1182
Ala Pro Gly Val Arg Gly Trp His Thr Thr Asp Asp Val Tyr Thr Ala
         255                 260                 265

CTG GGC TCG GCG GGG CTC TAC CGC ACG GGC ACC TCT GTG AAC TGC ATC         1230
Leu Gly Ser Ala Gly Leu Tyr Arg Thr Gly Thr Ser Val Asn Cys Ile
270                 275                 280

GTG GAA GAA GTG GAG GCG CGC TCG GTG TAC CCG TAC GAC TCG TTC GCG         1278
Val Glu Glu Val Glu Ala Arg Ser Val Tyr Pro Tyr Asp Ser Phe Ala
```

-continued

| | | | | | | | | | | | | | | | | |
|---|---|---|---|---|---|---|---|---|---|---|---|---|---|---|---|---|
| 285 | | | | | 290 | | | | | 295 | | | | | 300 | |
| CTC | TCG | ACC | GGG | GAC | ATT | ATC | TAC | ATG | TCG | CCC | TTT | TAC | GGG | CTG | CGC | 1326 |
| Leu | Ser | Thr | Gly | Asp 305 | Ile | Ile | Tyr | Met | Ser 310 | Pro | Phe | Tyr | Gly | Leu 315 | Arg | |
| GAG | GGC | GCG | CAC | CGC | GAG | CAC | ACC | AGC | TAC | TCG | CCG | GAG | CGC | TTC | CAG | 1374 |
| Glu | Gly | Ala | His 320 | Arg | Glu | His | Thr | Ser | Tyr 325 | Ser | Pro | Glu | Arg 330 | Phe | Gln | |
| CAG | ATC | GAG | GGC | TAC | TAC | AAG | CGC | GAC | ATG | GCC | ACG | GGC | CGG | CGC | CTC | 1422 |
| Gln | Ile | Glu 335 | Gly | Tyr | Tyr | Lys | Arg 340 | Asp | Met | Ala | Thr | Gly 345 | Arg | Arg | Leu | |
| AAG | GAG | CCG | GTC | TCG | CGG | AAC | TTT | TTG | CGT | ACA | CAG | CAC | GTG | ACG | GTA | 1470 |
| Lys | Glu 350 | Pro | Val | Ser | Arg | Asn 355 | Phe | Leu | Arg | Thr | Gln 360 | His | Val | Thr | Val | |
| GCC | TGG | GAC | TGG | GTG | CCC | AAG | CGC | AAA | AAC | GTG | TGC | TCG | CTG | GCC | AAG | 1518 |
| Ala 365 | Trp | Asp | Trp | Val | Pro 370 | Lys | Arg | Lys | Asn | Val 375 | Cys | Ser | Leu | Ala | Lys 380 | |
| TGG | CGC | GAG | GCG | GAC | GAA | ATG | CTG | CGA | GAC | GAG | AGC | CGC | GGG | AAC | TTC | 1566 |
| Trp | Arg | Glu | Ala | Asp 385 | Glu | Met | Leu | Arg | Asp 390 | Glu | Ser | Arg | Gly | Asn 395 | Phe | |
| CGC | TTC | ACG | GCC | CGC | TCG | CTC | TCG | GCG | ACC | TTT | GTG | AGC | GAC | AGC | CAC | 1614 |
| Arg | Phe | Thr | Ala 400 | Arg | Ser | Leu | Ser | Ala 405 | Thr | Phe | Val | Ser | Asp 410 | Ser | His | |
| ACC | TTC | GCG | TTG | CAG | AAT | GTG | CCG | CTG | AGC | GAC | TGC | GTG | ATC | GAA | GAG | 1662 |
| Thr | Phe | Ala 415 | Leu | Gln | Asn | Val | Pro 420 | Leu | Ser | Asp | Cys | Val 425 | Ile | Glu | Glu | |
| GCC | GAG | GCC | GCG | GTC | GAG | CGC | GTC | TAC | CGC | GAG | CGC | TAC | AAC | GGC | ACG | 1710 |
| Ala | Glu 430 | Ala | Ala | Val | Glu | Arg 435 | Val | Tyr | Arg | Glu | Arg 440 | Tyr | Asn | Gly | Thr | |
| CAC | GTG | CTG | TCG | GGC | AGC | TTG | GAG | ACG | TAC | CTG | GCG | CGC | GGC | GGC | TTT | 1758 |
| His 445 | Val | Leu | Ser | Gly | Ser 450 | Leu | Glu | Thr | Tyr | Leu 455 | Ala | Arg | Gly | Gly | Phe 460 | |
| GTC | GTG | GCC | TTC | CGG | CCG | ATG | CTC | AGC | AAC | GAG | CTG | GCC | AAG | CTG | TAC | 1806 |
| Val | Val | Ala | Phe | Arg 465 | Pro | Met | Leu | Ser | Asn 470 | Glu | Leu | Ala | Lys | Leu 475 | Tyr | |
| CTG | CAG | GAG | CTG | GCG | CGC | TCG | AAC | GGC | ACG | CTC | GAG | GGG | CTG | TTC | GCC | 1854 |
| Leu | Gln | Glu | Leu 480 | Ala | Arg | Ser | Asn | Gly 485 | Thr | Leu | Glu | Gly | Leu 490 | Phe | Ala | |
| GCC | GCG | GCG | CCC | AAG | CCG | GGC | CCG | CGG | CGC | GCG | CGC | CGG | CCG | CGC | CGT | 1902 |
| Ala | Ala | Ala 495 | Pro | Lys | Pro | Gly | Pro 500 | Arg | Arg | Ala | Arg | Arg 505 | Pro | Arg | Arg | |
| CTG | CGC | CCG | GCG | CCC | GGG | CGC | GGC | CAA | CGC | GCC | CGG | CGA | CGG | CAC | | 1950 |
| Leu | Arg 510 | Pro | Ala | Pro | Gly 515 | Arg | Gly | Gln | Arg | Ala 520 | Arg | Arg | Arg | His | | |
| GCC | GGC | GGG | CGG | GTG | ACT | ACC | GTG | AGC | CTG | GCC | GAG | TTT | GCG | GCG | CTG | 1998 |
| Ala 525 | Gly | Gly | Arg | Val | Thr 530 | Thr | Val | Ser | Ser | Ala 535 | Glu | Phe | Ala | Ala | Leu 540 | |
| CAG | TTC | ACT | CAC | GAC | CAT | ACC | AGG | ACC | AGT | GAA | CAC | CAT | GTT | CAC | CGC | 2046 |
| Gln | Phe | Thr | His | Asp 545 | His | Thr | Arg | Thr | Ser 550 | Glu | His | His | Val | His 555 | Arg | |
| CTG | GCC | AGT | CCC | TGG | TGC | CTG | CTG | CAG | AAC | AAG | GAG | CGC | GCC | CTG | TGG | 2094 |
| Leu | Ala | Ser | Pro 560 | Trp | Cys | Leu | Leu | Gln 565 | Asn | Lys | Glu | Arg | Ala 570 | Leu | Trp | |
| GCC | GAG | GCG | GCT | AAG | CTC | AAC | CCC | AGC | GCG | GCG | GCC | AGC | GCT | GCG | CTG | 2142 |
| Ala | Glu | Ala 575 | Ala | Lys | Leu | Asn | Pro 580 | Ser | Ala | Ala | Ala | Ser 585 | Ala | Ala | Leu | |
| GAC | CGC | CGG | CCG | CCG | CGC | GCA | TGT | TGG | GGG | ACG | CAT | GGC | CGT | GAC | GTA | 2190 |
| Asp | Arg | Arg 590 | Pro | Pro | Arg | Ala 595 | Cys | Trp | Gly | Thr | His 600 | Gly | Arg | Asp | Val | |
| CTG | CCA | CGA | GCT | GGG | CGA | GGG | GCG | CTG | TTC | ATC | GAG | AAC | TCG | AAT | GCG | 2238 |

| | | | | | | | | | | | | | | | | |
|---|---|---|---|---|---|---|---|---|---|---|---|---|---|---|---|---|
| Leu | Pro | Arg | Ala | Gly | Arg | Gly | Ala | Leu | Phe | Ile | Glu | Asn | Ser | Asn | Ala | |
| 605 | | | | 610 | | | | | 615 | | | | | 620 | | |
| CGC | GCC | CGG | CGG | CGT | TTG | CTA | CAG | CCG | CCG | CGG | TTC | CTT | TCC | TTC | GGC | 2286 |
| Arg | Ala | Arg | Arg | Arg | Leu | Leu | Gln | Pro | Pro | Arg | Phe | Leu | Ser | Phe | Gly | |
| | | | 625 | | | | | 630 | | | | | 635 | | | |
| AAC | GAG | AGC | GAG | CCG | GTG | GAG | GGC | CAG | CTC | GGC | GAG | GAC | AAC | GAG | CTG | 2334 |
| Asn | Glu | Ser | Glu | Pro | Val | Glu | Gly | Gln | Leu | Gly | Glu | Asp | Asn | Glu | Leu | |
| | | | 640 | | | | | 645 | | | | | 650 | | | |
| CTG | CCG | GGC | CGC | GAG | CTC | GTG | GAG | CCC | TGC | ACC | GCC | AAC | CAC | AAG | CGC | 2382 |
| Leu | Pro | Gly | Arg | Glu | Leu | Val | Glu | Pro | Cys | Thr | Ala | Asn | His | Lys | Arg | |
| | | 655 | | | | | 660 | | | | | 665 | | | | |
| TAC | TTC | CGC | TTT | GGC | GCG | GAC | TAC | GTG | TAC | TAC | GAG | AAC | TAC | GCG | TAC | 2430 |
| Tyr | Phe | Arg | Phe | Gly | Ala | Asp | Tyr | Val | Tyr | Tyr | Glu | Asn | Tyr | Ala | Tyr | |
| 670 | | | | | 675 | | | | | 680 | | | | | | |
| GTG | CGG | CGG | GTC | CCG | CTC | GCG | GAG | CTG | GAG | GTG | ATC | AGC | ACC | TTT | GTG | 2478 |
| Val | Arg | Arg | Val | Pro | Leu | Ala | Glu | Leu | Glu | Val | Ile | Ser | Thr | Phe | Val | |
| 685 | | | | | 690 | | | | | 695 | | | | | 700 | |
| GAC | CTA | AAC | CTC | ACG | GTT | CTG | GAG | GAC | CGC | GAG | TTC | TTG | CCG | CTA | GAA | 2526 |
| Asp | Leu | Asn | Leu | Thr | Val | Leu | Glu | Asp | Arg | Glu | Phe | Leu | Pro | Leu | Glu | |
| | | | | 705 | | | | | 710 | | | | | 715 | | |
| GTG | TAC | ACG | CGC | GCC | GAG | CTC | GCC | GAC | ACG | GGT | CTG | CTC | GAC | TAC | AGC | 2574 |
| Val | Tyr | Thr | Arg | Ala | Glu | Leu | Ala | Asp | Thr | Gly | Leu | Leu | Asp | Tyr | Ser | |
| | | | 720 | | | | | 725 | | | | | 730 | | | |
| GAG | ATA | CAG | CGC | CGC | AAC | CAG | CTG | CAC | GAG | CTC | CGG | TTC | TAC | GAC | ATT | 2622 |
| Glu | Ile | Gln | Arg | Arg | Asn | Gln | Leu | His | Glu | Leu | Arg | Phe | Tyr | Asp | Ile | |
| | | 735 | | | | | 740 | | | | | 745 | | | | |
| GAC | CGC | GTG | GTC | AAG | ACG | GAC | GGC | AAT | ATG | GCC | ATC | ATG | CGA | GGG | CTC | 2670 |
| Asp | Arg | Val | Val | Lys | Thr | Asp | Gly | Asn | Met | Ala | Ile | Met | Arg | Gly | Leu | |
| | 750 | | | | | 755 | | | | | 760 | | | | | |
| GCC | AAC | TTC | TTT | CAG | GGC | CTG | GGC | GCC | GTC | GGG | CAG | GCG | GTG | GGC | ACG | 2718 |
| Ala | Asn | Phe | Phe | Gln | Gly | Leu | Gly | Ala | Val | Gly | Gln | Ala | Val | Gly | Thr | |
| 765 | | | | | 770 | | | | | 775 | | | | | 780 | |
| GTG | GTG | CTG | GGC | GCC | GCG | GGT | GCC | GCG | CTC | TCG | ACC | GTG | TCG | GGC | ATC | 2766 |
| Val | Val | Leu | Gly | Ala | Ala | Gly | Ala | Ala | Leu | Ser | Thr | Val | Ser | Gly | Ile | |
| | | | | 785 | | | | | 790 | | | | | 795 | | |
| GCC | TCG | TTT | ATT | GCG | AAC | CCG | TTC | GGC | GCG | CTG | GCC | ACG | GGG | CTG | CTG | 2814 |
| Ala | Ser | Phe | Ile | Ala | Asn | Pro | Phe | Gly | Ala | Leu | Ala | Thr | Gly | Leu | Leu | |
| | | | 800 | | | | | 805 | | | | | 810 | | | |
| GTG | CTC | GCC | GGG | CTG | GTG | GCC | GCT | TTC | CTG | GCG | TAC | CGG | TAC | ATT | TCC | 2862 |
| Val | Leu | Ala | Gly | Leu | Val | Ala | Ala | Phe | Leu | Ala | Tyr | Arg | Tyr | Ile | Ser | |
| | | 815 | | | | | 820 | | | | | 825 | | | | |
| CGC | CTC | CGC | AGC | AAC | CCC | ATG | AAG | GCG | CTG | TAC | CCG | ATC | ACC | ACG | CGC | 2910 |
| Arg | Leu | Arg | Ser | Asn | Pro | Met | Lys | Ala | Leu | Tyr | Pro | Ile | Thr | Thr | Arg | |
| | 830 | | | | | 835 | | | | | 840 | | | | | |
| GCG | CTC | AAG | GAC | GAC | CCG | GGG | CGC | AAC | CGC | CCG | GGC | GAG | GAA | GAG | GAG | 2958 |
| Ala | Leu | Lys | Asp | Asp | Pro | Gly | Arg | Asn | Arg | Pro | Gly | Glu | Glu | Glu | Glu | |
| 845 | | | | | 850 | | | | | 855 | | | | | 860 | |
| GAG | TTT | GAC | GCG | GCC | AAA | CTG | GAG | CAG | GCC | CGC | GAG | ATG | ATC | AAG | TAT | 3006 |
| Glu | Phe | Asp | Ala | Ala | Lys | Leu | Glu | Gln | Ala | Arg | Glu | Met | Ile | Lys | Tyr | |
| | | | | 865 | | | | | 870 | | | | | 875 | | |
| ATG | TCG | CTC | GTG | TCA | GCG | GTC | GAG | CGG | CAA | GAG | CAC | AAG | GCG | AAA | AAG | 3054 |
| Met | Ser | Leu | Val | Ser | Ala | Val | Glu | Arg | Gln | Glu | His | Lys | Ala | Lys | Lys | |
| | | | 880 | | | | | 885 | | | | | 890 | | | |
| AGC | AAC | AAG | GCG | GCC | CGC | CTG | CTG | GCG | ACC | CGG | CTG | ACG | CAG | CTC | GCG | 3102 |
| Ser | Asn | Lys | Ala | Ala | Arg | Leu | Leu | Ala | Thr | Arg | Leu | Thr | Gln | Leu | Ala | |
| | | 895 | | | | | 900 | | | | | 910 | | | | |
| CTT | CGG | CGG | CGA | GCG | CCG | CCG | GAG | TAC | CAG | CAG | CTT | CCG | ATG | GCC | GAC | 3150 |
| Leu | Arg | Arg | Arg | Ala | Pro | Pro | Glu | Tyr | Gln | Gln | Leu | Pro | Met | Ala | Asp | |
| | 915 | | | | | 920 | | | | | 925 | | | | | |

-continued

```
GTC  CGG  GGG  GCA  TGAGGCCTAT  GTATGGGCAG  TTCGGGTGCC  AATAATAAAT              3202
Val  Gly  Gly  Ala
930

TTTGCGCGAA  TCTTATTTAA  GTGCACACCG  TGTTATTTGC  GGCTGTTTGT  TTTTCCTGGA          3262

GGCGGGACTG  CGCGCGAGCT  CGGCCGGATT  AGGGTTCGGC  GCCACCCGGG  CACGGCAGGG          3322

CGCCCTTTAC  TTATGTTTGG  CGCGCGGTGG  CTCCGGCACC  GGTCTCTGTG  GCCCTCCCCC          3382

CGCCTTTGCG  TTTATTGGTC  CCAGCTGTGT  TCCCGCCTTT  GCGTGCCCCC  CGCCCGAGCG          3442

CCCGACCGTC  CTTCCCCGCC  CGACCGTCCT  TCCCGGCGCG  CCTCCTCCCG  CGCCACAAAG          3502

CACATTTGAC  CCCAAAA                                                            3519
```

( 2 ) INFORMATION FOR SEQ ID NO:2:

( i ) SEQUENCE CHARACTERISTICS:
        ( A ) LENGTH: 1829 base pairs
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
        ( A ) ORGANISM: bovine herpervirus- 1
        ( B ) INDIVIDUAL ISOLATE: Cooper strain ( v i i ) FEATURE:
        ( A ) NAME/KEY: coding sequence for gIII glycoprotein
        ( B ) LOCATION: 153 to 1722
        ( C ) IDENTIFICATION METHOD: sequence analysis ( x ) PUBLICATION INFORMATION:
        ( A ) AUTHORS: Fitzpatrick, David R.
                    Babuik, Lorne A.
                    Zamb, Tim j.
        ( B ) TITLE: Nucleotide Sequence of Bovine Herpesvirus Type etc
        ( C ) JOURNAL: Virology
        ( D ) VOLUME: 173
        ( F ) PAGES: 46-57
        ( G ) DATE: 1989
        ( K ) RELEVANT RESIDUES IN SEQ ID NO:2: FROM 153 TO 1722

( x i ) SEQUENCE DESCRIPTION:SEQ ID NO:2:

```
CGCGCCTGCA  GCCGCGCGTG  TGCTCAATCC  CGGACCACGA  AAGCACAAAA  CGGACGCCCT           60

TAAAAATGTA  GCCCGCGCCG  CGGTCGCGGC  CATCTTGGAT  CCACCCGCGC  GCACGACCGC          120

CGAGAGACCG  CCAGCCCGAG  ACCTCGCCGC  GCGTCCGCC  ATG  GGC  CCG  CTG  GGG  CGA     177
                                              Met  Gly  Pro  Leu  Gly  Arg
                                                                        5

GCG  TGG  CTG  ATC  GCA  GCT  ATT  TTC  GCC  TGG  GCG  CTC  CTG  TCT  GCC  CGG  225
Ala  Trp  Leu  Ile  Ala  Ala  Ile  Phe  Ala  Trp  Ala  Leu  Leu  Ser  Ala  Arg
               10                        15                        20

CGG  GGG  CTC  GCC  GAG  GAG  GCG  GAA  GCC  TCG  CCC  TCG  CCT  CCG  CCC  TCC  273
Arg  Gly  Leu  Ala  Glu  Glu  Ala  Glu  Ala  Ser  Pro  Ser  Pro  Pro  Pro  Ser
          25                        30                        35

CCG  TGC  CCA  ACC  GAG  ACG  GAA  AGC  TCC  GCT  GGG  ACC  ACC  GGC  GCA  ACG  321
Pro  Cys  Pro  Thr  Glu  Thr  Glu  Ser  Ser  Ala  Gly  Thr  Thr  Gly  Ala  Thr
     40                        45                        50

CCC  CCC  ACG  CCC  AAC  AGC  CCC  GAC  GCT  ACG  CCA  GAG  GAC  AGC  ACG  CCC  369
Pro  Pro  Thr  Pro  Asn  Ser  Pro  Asp  Ala  Thr  Pro  Glu  Asp  Ser  Thr  Pro
55                        60                        65                        70

GGT  GCT  ACT  ACG  CCC  GTG  GGG  ACG  CCG  GAG  CCG  CCG  TCC  GTG  TCC  GAG  417
Gly  Ala  Thr  Thr  Pro  Val  Gly  Thr  Pro  Glu  Pro  Pro  Ser  Val  Ser  Glu
```

-continued

|  |  |  | 75 |  |  |  |  | 80 |  |  |  |  | 85 |  |  |  |
|---|---|---|---|---|---|---|---|---|---|---|---|---|---|---|---|---|
| CAC | GAC | CCG | CCC | GTT | ACC | AAC | AGC | ACG | CCG | CCG | CCC | GCC | CCG | CCC | GAG | 465 |
| His | Asp | Pro | Pro | Val | Thr | Asn | Ser | Thr | Pro | Pro | Pro | Ala | Pro | Pro | Glu |  |
|  |  |  | 90 |  |  |  |  | 95 |  |  |  |  | 100 |  |  |  |
| GAC | GGG | CGA | CCC | GGC | GGC | GCT | GGC | AAC | GCG | AGC | CGC | GAT | GGG | CGA | CCT | 513 |
| Asp | Gly | Arg | Pro | Gly | Gly | Ala | Gly | Asn | Ala | Ser | Arg | Asp | Gly | Arg | Pro |  |
|  |  | 105 |  |  |  |  | 110 |  |  |  |  | 115 |  |  |  |  |
| AGC | GGC | GGG | GGG | CGG | CCT | CGC | CCC | CCG | CGG | CCG | AGC | AAA | GCC | CCG | CCG | 561 |
| Ser | Gly | Gly | Gly | Arg | Pro | Arg | Pro | Pro | Arg | Pro | Ser | Lys | Ala | Pro | Pro |  |
|  | 120 |  |  |  |  | 125 |  |  |  |  | 130 |  |  |  |  |  |
| AAG | GAG | CGC | AAG | TGG | ATG | CTC | TGC | GAG | CGC | GAG | GCC | GTG | GCC | GCC | TCG | 609 |
| Lys | Glu | Arg | Lys | Trp | Met | Leu | Cys | Glu | Arg | Glu | Ala | Val | Ala | Ala | Ser |  |
| 135 |  |  |  | 140 |  |  |  |  | 145 |  |  |  |  | 150 |  |  |
| TAC | GCC | GAG | CCG | CTG | TAC | GTG | CAC | TGC | GGC | GTG | GCC | GAC | AAC | GCC | ACT | 657 |
| Tyr | Ala | Glu | Pro | Leu | Tyr | Val | His | Cys | Gly | Val | Ala | Asp | Asn | Ala | Thr |  |
|  |  |  |  | 155 |  |  |  |  | 160 |  |  |  |  | 165 |  |  |
| GGC | GGT | GCG | CGC | CTG | GAG | CTC | TGG | TTT | CAG | CGC | GTG | GGC | AGG | TTC | CGC | 705 |
| Gly | Gly | Ala | Arg | Leu | Glu | Leu | Trp | Phe | Gln | Arg | Val | Gly | Arg | Phe | Arg |  |
|  |  |  | 170 |  |  |  |  | 175 |  |  |  |  | 180 |  |  |  |
| TCC | ACG | CGC | GGC | GAC | GAC | GAG | GCC | GTG | CGC | AAC | CCC | TTT | CCG | CGG | GCC | 753 |
| Ser | Thr | Arg | Gly | Asp | Asp | Glu | Ala | Val | Arg | Asn | Pro | Phe | Pro | Arg | Ala |  |
|  |  | 185 |  |  |  |  | 190 |  |  |  |  | 195 |  |  |  |  |
| CCG | CCC | GTG | CTG | CTG | TTC | GTA | GCC | CAG | AAC | GGC | TCG | ATC | GCG | TAC | CGT | 801 |
| Pro | Pro | Val | Leu | Leu | Phe | Val | Ala | Gln | Asn | Gly | Ser | Ile | Ala | Tyr | Arg |  |
|  | 200 |  |  |  |  | 205 |  |  |  |  | 210 |  |  |  |  |  |
| AGC | GCG | GAG | CTG | GGC | GAC | AAC | TAT | ATT | TTC | CCT | TCG | CCC | GCC | GAC | CCC | 849 |
| Ser | Ala | Glu | Leu | Gly | Asp | Asn | Tyr | Ile | Phe | Pro | Ser | Pro | Ala | Asp | Pro |  |
| 215 |  |  |  | 220 |  |  |  |  | 225 |  |  |  |  | 230 |  |  |
| CGC | AAC | TTG | CCC | CTG | ACC | GTG | CGC | TCC | CTG | ACG | GCC | GCC | ACC | GAG | GGC | 897 |
| Arg | Asn | Leu | Pro | Leu | Thr | Val | Arg | Ser | Leu | Thr | Ala | Ala | Thr | Glu | Gly |  |
|  |  |  |  | 235 |  |  |  |  | 240 |  |  |  |  | 245 |  |  |
| GTG | TAC | ACT | TGG | CGC | CGC | GAC | ATG | GGC | ACC | AAG | TCA | CAG | CGC | AAG | GTC | 945 |
| Val | Tyr | Thr | Trp | Arg | Arg | Asp | Met | Gly | Thr | Lys | Ser | Gln | Arg | Lys | Val |  |
|  |  |  | 250 |  |  |  |  | 255 |  |  |  |  | 260 |  |  |  |
| GTG | ACC | GTC | ACG | ACG | CAC | CGC | GCG | CCC | GCT | GTT | TCC | GTC | GAA | CCC | CAG | 993 |
| Val | Thr | Val | Thr | Thr | His | Arg | Ala | Pro | Ala | Val | Ser | Val | Glu | Pro | Gln |  |
|  |  | 265 |  |  |  |  | 270 |  |  |  |  | 275 |  |  |  |  |
| CCA | GCG | CTA | GAA | GGC | GCC | GGC | TAC | GCG | GCC | GTG | TGC | CGC | GCC | GCC | GAG | 1041 |
| Pro | Ala | Leu | Glu | Gly | Ala | Gly | Tyr | Ala | Ala | Val | Cys | Arg | Ala | Ala | Glu |  |
| 280 |  |  |  |  | 285 |  |  |  |  | 290 |  |  |  |  |  |  |
| TAC | TAC | CCG | CCG | CGC | TCC | ACG | CGC | CTG | CAC | TGG | TTC | CGC | AAC | GGC | TAC | 1089 |
| Tyr | Tyr | Pro | Pro | Arg | Ser | Thr | Arg | Leu | His | Trp | Phe | Arg | Asn | Gly | Tyr |  |
| 295 |  |  |  |  | 300 |  |  |  |  | 305 |  |  |  |  | 310 |  |
| CCC | GTG | GAG | GCT | CGG | CAC | GCG | CGC | GAC | GTC | TTT | ACG | GTC | GAC | GAC | TCC | 1137 |
| Pro | Val | Glu | Ala | Arg | His | Ala | Arg | Asp | Val | Phe | Thr | Val | Asp | Asp | Ser |  |
|  |  |  |  | 315 |  |  |  |  | 320 |  |  |  |  | 325 |  |  |
| GGG | CTC | TTT | TCG | CGC | ACG | TCC | GTC | CTT | ACG | CTC | GAG | GAC | GCG | ACG | CCA | 1185 |
| Gly | Leu | Phe | Ser | Arg | Thr | Ser | Val | Leu | Thr | Leu | Glu | Asp | Ala | Thr | Pro |  |
|  |  |  | 330 |  |  |  |  | 335 |  |  |  |  | 340 |  |  |  |
| ACC | GCC | CAC | CCG | CCC | AAC | CTG | CGC | TGC | GAC | GTC | TCC | TGG | TTC | CAG | AGC | 1233 |
| Thr | Ala | His | Pro | Pro | Asn | Leu | Arg | Cys | Asp | Val | Ser | Trp | Phe | Gln | Ser |  |
|  |  | 345 |  |  |  |  | 350 |  |  |  |  | 355 |  |  |  |  |
| GCT | AAC | ATG | GAG | CGC | CGC | TTT | TAC | GCG | GCT | GGC | ACG | CCG | GCC | GTT | TAC | 1281 |
| Ala | Asn | Met | Glu | Arg | Arg | Phe | Tyr | Ala | Ala | Gly | Thr | Pro | Ala | Val | Tyr |  |
| 360 |  |  |  |  | 365 |  |  |  |  | 370 |  |  |  |  |  |  |
| CGC | CCG | CCC | GAG | CTG | CGC | GTG | TAC | TTC | GAG | GGC | GGC | GAG | GCC | GTC | TGC | 1329 |
| Arg | Pro | Pro | Glu | Leu | Arg | Val | Tyr | Phe | Glu | Gly | Gly | Glu | Ala | Val | Cys |  |
| 375 |  |  |  |  | 380 |  |  |  |  | 385 |  |  |  |  | 390 |  |
| GAG | GCG | CGC | TGC | GTC | CCC | GAG | GGG | CGC | GTC | TCC | CTG | CGC | TGG | ACG | GTG | 1377 |

| | | | | | | | | | | | | | | | |
|---|---|---|---|---|---|---|---|---|---|---|---|---|---|---|---|
| Glu | Ala | Arg | Cys | Val 395 | Pro | Glu | Gly | Arg | Val 400 | Ser | Leu | Arg | Trp | Thr 405 | Val |

| | | | | | | | | | | | | | | | | |
|---|---|---|---|---|---|---|---|---|---|---|---|---|---|---|---|---|
| CGC | GAC | GGC | ATC | GCC | CCG | TCG | CGC | ACT | GAG | CAG | ACC | GGC | GTC | TGC | GCC | 1425 |
| Arg | Asp | Gly | Ile 410 | Ala | Pro | Ser | Arg | Thr 415 | Glu | Gln | Thr | Gly | Val 420 | Cys | Ala | |
| GAG | CGG | CCC | GGG | CTG | GTA | AAC | CTG | CGC | GGC | GTG | CGC | CTG | CTT | TCT | ACA | 1473 |
| Glu | Arg | Pro 425 | Gly | Leu | Val | Asn | Leu 430 | Arg | Gly | Val | Arg | Leu 435 | Leu | Ser | Thr | |
| ACC | GAC | GGG | CCC | GTC | GAC | TAC | ACC | TGC | ACC | GCC | ACT | GGC | TAC | CCG | GCA | 1521 |
| Thr | Asp 440 | Gly | Pro | Val | Asp | Tyr 445 | Thr | Cys | Thr | Ala | Thr 450 | Gly | Tyr | Pro | Ala | |
| CCG | CTG | CCC | GAG | TTC | TCC | GCG | ACC | GCC | ACG | TAC | GAC | GCC | TCG | CCC | GGC | 1569 |
| Pro 455 | Leu | Pro | Glu | Phe | Ser 460 | Ala | Thr | Ala | Thr | Tyr 465 | Asp | Ala | Ser | Pro | Gly 470 | |
| CTA | ATC | GGA | AGC | CCC | GTC | CTC | GTC | AGC | GTC | GTG | GCC | GTC | GCC | TGC | GGT | 1617 |
| Leu | Ile | Gly | Ser | Pro 475 | Val | Leu | Val | Ser | Val 480 | Val | Ala | Val | Ala | Cys 485 | Gly | |
| CTC | GGC | GCC | GTG | GGG | CTC | CTG | CTG | GTG | GCG | GCC | TCG | TGC | CTG | CGG | CGC | 1665 |
| Leu | Gly | Ala | Val 490 | Gly | Leu | Leu | Leu | Val 495 | Ala | Ala | Ser | Cys | Leu 500 | Arg | Arg | |
| AAG | GCC | CGG | GTA | ATC | CAA | CCC | GGT | CTT | ACT | CGC | GCT | CGC | GCC | CTC | GGC | 1713 |
| Lys | Ala | Arg 505 | Val | Ile | Gln | Pro | Gly 510 | Leu | Thr | Arg | Ala | Arg 515 | Ala | Leu | Gly | |
| TCC | GCG | CCC | TAG | ACGACCGGCA | CGGCCTGGAG | GCGCTGGCGG | CTGCCGGTGC | | | | | | | | | 1765 |
| Ser | Ala | Pro 520 | | | | | | | | | | | | | | |

CGCTCACACC GCGCGCCACA ACCGCGACGT GTGGCAGCGC TTTTCCCGCG TCTGCGAGGC 1825

CGGC 1829

( 2 ) INFORMATION FOR SEQ ID NO:3:

( i ) SEQUENCE CHARACTERISTICS:
        ( A ) LENGTH: 1405 base pairs
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
        ( A ) ORGANISM: bovine herpervirus- 1
        ( B ) INDIVIDUAL ISOLATE: Cooper strain ( v i i ) FEATURE:
        ( A ) NAME/KEY: coding sequence for gIV glycoprotein
        ( B ) LOCATION: 85 to 1339
        ( C ) IDENTIFICATION METHOD: sequence analysis ( x ) PUBLICATION INFORMATION:
        ( A ) AUTHORS: Tikoo, Suresh K.
                Fitzpatrick, David R.
                Babuik, Lorne A.
                Zamb, Tim j.
        ( B ) TITLE: Molecular Cloning, Sequencing, and Expression etc
        ( C ) JOURNAL: Journal of Virology
        ( D ) VOLUME: 64
        ( E ) ISSUE: 10
        ( F ) PAGES: 5132-3142
        ( G ) DATE: October, 1990
        ( K ) RELEVANT RESIDUES IN SEQ ID NO:3: FROM 85 TO 1339

( x i ) SEQUENCE DESCRIPTION:SEQ ID NO:3:

GGGCCGCAGC CCCGGCTGGG TATATATCCC CGACGGGCGA CTAGAGATAC ACTCGCCCCG 60

-continued

| | | | | | | | | | | | | | | | | |
|---|---|---|---|---|---|---|---|---|---|---|---|---|---|---|---|---|
| CGCGGCTGCT | GCGAGCGGGC | GAAC | ATG | CAA | GGG | CCG | ACA | TTG | GCC | GTG | CTG | | | | | 111 |
| | | | Met | Gln | Gly | Pro | Thr | Leu | Ala | Val | Leu | | | | | |
| | | | | | | | | 5 | | | | | | | | |
| GGC | GCG | CTG | CTC | GCC | GTT | GCG | GTG | AGC | TTG | CCT | ACA | CCC | GCG | CCG | CGG | 159 |
| Gly | Ala | Leu | Leu | Ala | Val | Ala | Val | Ser | Leu | Pro | Thr | Pro | Ala | Pro | Arg | |
| 10 | | | | 15 | | | | 20 | | | | | | 25 | | |
| GTG | ACG | GTA | TAC | GTC | GAC | CCG | CCG | GCG | TAC | CCG | ATG | CCG | CGA | TAC | AAC | 207 |
| Val | Thr | Val | Tyr | Val | Asp | Pro | Pro | Ala | Tyr | Pro | Met | Pro | Arg | Tyr | Asn | |
| | | | | 30 | | | | 35 | | | | | 40 | | | |
| TAC | ACT | GAA | CGC | TGG | CAC | ACT | ACC | GGG | CCC | ATA | CCG | TCG | CCC | TTC | GCA | 255 |
| Tyr | Thr | Glu | Arg | Trp | His | Thr | Thr | Gly | Pro | Ile | Pro | Ser | Pro | Phe | Ala | |
| | | | 45 | | | | | 50 | | | | | 55 | | | |
| GAC | GGC | CGC | GAG | CAG | CCC | GTC | GAG | GTG | CGC | TAC | GCG | ACG | AGC | GCG | GCG | 303 |
| Asp | Gly | Arg | Glu | Gln | Pro | Val | Glu | Val | Arg | Tyr | Ala | Thr | Ser | Ala | Ala | |
| | | 60 | | | | | 65 | | | | | 70 | | | | |
| GCG | TGC | GAC | ATG | CTG | GCG | CTG | ATC | GCA | GAC | CCG | CAG | GTG | GGG | CGC | ACG | 351 |
| Ala | Cys | Asp | Met | Leu | Ala | Leu | Ile | Ala | Asp | Pro | Gln | Val | Gly | Arg | Thr | |
| | 75 | | | | 80 | | | | | 85 | | | | | | |
| CTG | TGG | GAA | GCG | GTA | CGC | CGG | CAC | GCG | CGC | GCG | TAC | AAC | GCC | ACG | GTC | 399 |
| Leu | Trp | Glu | Ala | Val | Arg | Arg | His | Ala | Arg | Ala | Tyr | Asn | Ala | Thr | Val | |
| 90 | | | | | 95 | | | | 100 | | | | | | 105 | |
| ATA | TGG | TAC | AAG | ATC | GAG | AGC | GGG | TGC | GCC | CGG | CCG | CTG | TAC | TAC | ATG | 447 |
| Ile | Trp | Tyr | Lys | Ile | Glu | Ser | Gly | Cys | Ala | Arg | Pro | Leu | Tyr | Tyr | Met | |
| | | | | 110 | | | | | 115 | | | | | 120 | | |
| GAG | TAC | ACC | GAG | TGC | GAG | CCC | AGG | AAG | CAC | TTT | GGG | TAC | TGC | CGC | TAC | 495 |
| Glu | Tyr | Thr | Glu | Cys | Glu | Pro | Arg | Lys | His | Phe | Gly | Tyr | Cys | Arg | Tyr | |
| | | | 125 | | | | | 130 | | | | | 135 | | | |
| CGC | ACA | CCC | CCG | TTT | TGG | GAC | AGC | TTC | CTG | GCG | GGC | TTC | GCC | TAC | CCC | 543 |
| Arg | Thr | Pro | Pro | Phe | Trp | Asp | Ser | Phe | Leu | Ala | Gly | Phe | Ala | Tyr | Pro | |
| | | 140 | | | | | 145 | | | | | 150 | | | | |
| ACG | GAC | GAC | GAG | CTG | GGA | CTG | ATT | ATG | GCG | GCG | CCC | GCG | CGG | CTC | GTC | 591 |
| Thr | Asp | Asp | Glu | Leu | Gly | Leu | Ile | Met | Ala | Ala | Pro | Ala | Arg | Leu | Val | |
| | 155 | | | | | 160 | | | | | 165 | | | | | |
| GAG | GGC | CAG | TAC | CGA | CGC | GCG | CTG | TAC | ATC | GAC | GGC | ACG | GTC | GCC | TAT | 639 |
| Glu | Gly | Gln | Tyr | Arg | Arg | Ala | Leu | Tyr | Ile | Asp | Gly | Thr | Val | Ala | Tyr | |
| 170 | | | | | 175 | | | | | 180 | | | | | 185 | |
| ACA | GAT | TTC | ATG | GTT | TCG | CTG | CCG | GCC | GGG | GAC | TGC | TGG | TTC | TCG | AAA | 687 |
| Thr | Asp | Phe | Met | Val | Ser | Leu | Pro | Ala | Gly | Asp | Cys | Trp | Phe | Ser | Lys | |
| | | | | 190 | | | | | 195 | | | | | 200 | | |
| CTC | GGC | GCG | GCT | CGC | GGG | TAC | ACC | TTT | GGC | GCG | TGC | TTC | CCG | GCC | CGG | 735 |
| Leu | Gly | Ala | Ala | Arg | Gly | Tyr | Thr | Phe | Gly | Ala | Cys | Phe | Pro | Ala | Arg | |
| | | | 205 | | | | | 210 | | | | | 215 | | | |
| GAT | TAC | GAG | CAA | AAG | AAG | GTT | CTG | CGC | CTG | ACG | TAT | CTC | ACG | CAG | TAC | 783 |
| Asp | Tyr | Glu | Gln | Lys | Lys | Val | Leu | Arg | Leu | Thr | Tyr | Leu | Thr | Gln | Tyr | |
| | | 220 | | | | | 225 | | | | | 230 | | | | |
| TAC | CCG | CAG | GAG | GCA | CAC | AAG | GCC | ATA | GTC | GAC | TAC | TGG | TTC | ATG | CGC | 831 |
| Tyr | Pro | Gln | Glu | Ala | His | Lys | Ala | Ile | Val | Asp | Tyr | Trp | Phe | Met | Arg | |
| | 235 | | | | | 240 | | | | | 245 | | | | | |
| CAC | GGG | GGC | GTC | GTT | CCG | CCG | TAT | TTT | GAG | GAG | TCG | AAG | GGC | TAC | GAG | 879 |
| His | Gly | Gly | Val | Val | Pro | Pro | Tyr | Phe | Glu | Glu | Ser | Lys | Gly | Tyr | Glu | |
| 250 | | | | | 255 | | | | | 260 | | | | | 265 | |
| CCG | CCG | CCT | GCC | GCC | GAT | GGG | GGT | TCC | CCC | GCG | CCA | CCC | GGC | GAC | GAC | 927 |
| Pro | Pro | Pro | Ala | Ala | Asp | Gly | Gly | Ser | Pro | Ala | Pro | Pro | Gly | Asp | Asp | |
| | | | | 270 | | | | | 275 | | | | | 280 | | |
| GAG | GCC | CGC | GAG | GAT | GAA | GGG | GAG | ACC | GAG | GAC | GGG | GCA | GCC | GGG | CGG | 975 |
| Glu | Ala | Arg | Glu | Asp | Glu | Gly | Glu | Thr | Glu | Asp | Gly | Ala | Ala | Gly | Arg | |
| | | | 285 | | | | | 290 | | | | | 295 | | | |
| GAG | GGC | AAC | GGC | GGC | CCC | CCA | GGA | CCC | GAA | GGC | GAC | GGC | GAG | AGT | CAG | 1023 |
| Glu | Gly | Asn | Gly | Gly | Pro | Pro | Gly | Pro | Glu | Gly | Asp | Gly | Glu | Ser | Gln | |

-continued

| | | 300 | | | | | | | | | | 305 | | | | | | | | 310 | | | |
|---|---|---|---|---|---|---|---|---|---|---|---|---|---|---|---|---|
| ACC | CCC | GAA | GCC | AAC | GGA | GGC | GCC | GAG | GGC | GAG | CCG | AAA | CCC | GGC | CCC | 1071 |
| Thr | Pro | Glu | Ala | Asn | Gly | Gly | Ala | Glu | Gly | Glu | Pro | Lys | Pro | Gly | Pro | |
| | 315 | | | | | 320 | | | | | 325 | | | | | |
| AGC | CCC | GAC | GCC | GAC | CGC | CCC | GAA | GGC | TGG | CCG | AGC | CTC | GAA | GCC | ATC | 1119 |
| Ser | Pro | Asp | Ala | Asp | Arg | Pro | Glu | Gly | Trp | Pro | Ser | Leu | Glu | Ala | Ile | |
| 330 | | | | | 335 | | | | | 340 | | | | | 345 | |
| ACG | CAC | CCC | CCG | CCC | GCC | CCC | GCT | ACG | CCC | GCG | GCC | CCC | GAC | GCC | GTG | 1167 |
| Thr | His | Pro | Pro | Pro | Ala | Pro | Ala | Thr | Pro | Ala | Ala | Pro | Asp | Ala | Val | |
| | | | 350 | | | | | 355 | | | | | 360 | | | |
| CCG | GTC | AGC | GTC | GGG | ATC | GGC | ATT | GCG | GCT | GCG | GCG | ATC | GCG | TGC | GTG | 1215 |
| Pro | Val | Ser | Val | Gly | Ile | Gly | Ile | Ala | Ala | Ala | Ala | Ile | Ala | Cys | Val | |
| | | 365 | | | | | 370 | | | | | 375 | | | | |
| GCC | GCC | GCC | GCC | GCC | GGC | GCG | TAC | TTC | GTC | TAT | ACG | CGC | CGG | CGC | GGT | 1263 |
| Ala | Ala | Ala | Ala | Ala | Gly | Ala | Tyr | Phe | Val | Tyr | Thr | Arg | Arg | Arg | Gly | |
| | | 380 | | | | | 385 | | | | | 390 | | | | |
| GCG | GGT | CCG | CTG | CCC | AGA | AAG | CCA | AAA | AAG | CTG | CCG | GCC | TTT | GGC | AAC | 1311 |
| Ala | Gly | Pro | Leu | Pro | Arg | Lys | Pro | Lys | Lys | Leu | Pro | Ala | Phe | Gly | Asn | |
| | 395 | | | | | 400 | | | | | 405 | | | | | |
| GTC | AAC | TAC | AGC | GCG | CTG | CCC | GGG | TGA | GCGGCCTAGG | CCCTCCCCG | | | | | | 1358 |
| Val | Asn | Tyr | Ser | Ala | Leu | Pro | Gly | | | | | | | | | |
| 410 | | | | | 415 | | | | | | | | | | | |

ACCGCCCCT TTGCTCCTAG CCCCGGCTCC TGCCGAGCCG CGCGGGG 1405